(12) United States Patent
Shelso

(10) Patent No.: US 6,929,635 B2
(45) Date of Patent: Aug. 16, 2005

(54) REINFORCED MULTI-LUMEN MEDICAL SHAFT

(75) Inventor: Susan I. Shelso, Plymouth, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 51 days.

(21) Appl. No.: 10/224,189

(22) Filed: Aug. 20, 2002

(65) Prior Publication Data
US 2004/0039369 A1 Feb. 26, 2004

(51) Int. Cl.[7] .................. A61M 37/00; A61M 29/00; A61M 25/00
(52) U.S. Cl. ............... 604/523; 604/525; 604/95.01; 604/94.01; 604/96.01; 600/434
(58) Field of Search ............... 604/94.01–96.01, 604/523–527, 103.09, 102.01, 131–132, 194, 67, 264, 31, 151, 102.02, 164.13; 600/434; 606/194

(56) References Cited

U.S. PATENT DOCUMENTS

| 5,057,092 | A |   | 10/1991 | Webster, Jr. |  |
|---|---|---|---|---|---|
| 5,063,018 | A |   | 11/1991 | Fontirroche et al. |  |
| 5,190,520 | A |   | 3/1993 | Fenton, Jr. et al. |  |
| 5,221,255 | A |   | 6/1993 | Mahurkar et al. |  |
| 5,281,203 | A |   | 1/1994 | Ressemann |  |
| 5,328,472 | A |   | 7/1994 | Steinke et al. |  |
| 5,542,937 | A |   | 8/1996 | Chee et al. |  |
| 5,695,483 | A |   | 12/1997 | Samson |  |
| 5,782,811 | A |   | 7/1998 | Samson et al. |  |
| 5,863,366 | A |   | 1/1999 | Snow |  |
| 5,957,899 | A | * | 9/1999 | Spears et al. | 604/264 |
| 5,980,484 | A |   | 11/1999 | Ressemann et al. |  |
| 6,004,310 | A |   | 12/1999 | Bardsley et al. |  |
| 6,036,670 | A | * | 3/2000 | Wijeratne et al. | 604/96.01 |
| 6,186,978 | B1 | * | 2/2001 | Samson et al. | 604/96.01 |
| 6,197,014 | B1 |   | 3/2001 | Samson et al. |  |
| 6,217,565 | B1 | * | 4/2001 | Cohen | 604/525 |
| 6,273,880 | B1 |   | 8/2001 | Berg et al. |  |
| 6,398,776 | B1 | * | 6/2002 | Sekino et al. | 604/524 |
| 6,575,958 | B1 | * | 6/2003 | Happ et al. | 604/525 |
| 6,733,487 | B2 | * | 5/2004 | Keith et al. | 604/526 |
| 2003/0004493 | A1 | * | 1/2003 | Casey et al. |  |

FOREIGN PATENT DOCUMENTS

| WO | WO 96/17644 | 6/1996 |
|---|---|---|
| WO | WO 07/48434 | 12/1997 |

OTHER PUBLICATIONS

International Search Report for related PCT Application No. PCT/US03/25920, report dated Dec. 29, 2003.

* cited by examiner

*Primary Examiner*—Nicholas D. Lucchesi
*Assistant Examiner*—Roz Maiorino
(74) *Attorney, Agent, or Firm*—Marshall, Gerstein & Borun LLP

(57) ABSTRACT

A medical shaft or tubing includes an elongate tubular member having a proximal end and a distal end. The shaft also includes a tubular wall extending between the proximal and distal ends to define a first lumen. The elongated tubular member further comprises a second lumen extending through at least a portion of the tubular member. The tubular wall additionally includes a reinforcing element that surrounds at least a portion of the first lumen and that surrounds and overlaps at least a portion of the second lumen.

15 Claims, 3 Drawing Sheets

REINFORCED MULTI-LUMEN MEDICAL SHAFT

TECHNICAL FIELD

An improved intravascular catheter or shaft is disclosed. More specifically, a reinforced, multi-lumen, intravascular catheter or shaft is disclosed.

BACKGROUND OF THE RELATED ART

Intravascular catheters are widely used for a variety of diagnostic and therapeutic purposes. Catheters are used to place various treatment materials, such as drugs and devices, within remote regions of the body. Specifically, in the treatment of the circulatory system via percutaneous transluminal angioplasty (PCTA) catheters are utilized having balloons on their distal ends. These catheters treat narrowed regions or stenoses in the vascular system by expanding the balloon in a region of the vessel having plaque build-up and pressing the plaque radially outward into the vessel wall. Angioplasty has been developed as an alternative to bypass surgery for treating vascular diseases or other conditions that cause occlusion or reduction of blood flow in a patient's vascular system.

To access and treat such vascular maladies, catheters are moved through the circulatory system to a selected site with the assistance of a guide wire. The guide wire may be fixedly attached to the catheter. Also, the guide wire may be slidably accommodated within the catheter. The guide wire may pass through the main lumen of the catheter or through a separate lumen that extends parallel to the main lumen of a multi-lumen catheter.

Multi-lumen catheters commonly include a main lumen and at least one secondary lumen. The main lumen is typically used for balloon inflation or deflation, irrigation, delivery of drugs or other treatments and to facilitate the insertion of other surgical devices, such as an angioscope. The secondary lumen is typically used for accommodating the guide wire.

Catheters having a separate, secondary, guide wire lumen extending throughout the length of the catheter are often referred to as "over-the-wire" catheters. Catheters having a guide wire lumen that only extends through the distal portion of the catheter are referred to as "single-operator-exchange" or "rapid exchange" catheters. The single operator exchange or rapid exchange catheters have a shortened guide wire lumen which extends from the distal end of the catheter to a location just proximal to a "payload" area, or the location of the treatment drug or device, such as a dilation balloon or a stent. Rapid exchange catheters advantageously reduce the amount of friction generated as the guide wire slides through the catheter and enhances the feel and responsiveness of the catheter to a physician.

Because it may be necessary for a catheter to access a remote site within the vascular system, catheters must pass through increasingly narrow and tortuous pathways with sharp bends and curves. To effectively traverse these remote pathways of the vasculature, catheters must be designed with certain key characteristics. First, the catheter assembly must have sufficient stiffness or "pushability" to enable a longitudinal force to be transmitted through the assembly so that the physician can advance or push the catheter through the vasculature to the site of a stenosis.

Secondly, the catheter must also be sufficiently flexible so that the catheter tip can pass through the sharp bends of the increasingly narrow blood vessels. This flexibility, often referred to as "trackability," allows the physician to manipulate the catheter through a patient's vascular system.

While there are a number of different ways in which catheters may be designed to have the desired pushability and trackability characteristics, many catheters are currently constructed with a reinforcing element. This reinforcing element typically includes a braided material or, sometimes, a spirally wound material. Braided reinforcement elements are particularly useful for providing axial strength to the exterior tube of a multi-lumen catheter because the multi-lumen catheter is particularly susceptible to kinking or ovalization of the circular cross-sections of the various lumens when the catheter is exposed to a high flexure or a high torsion, such as when the catheter is passed through the bends or turns of the vascular system.

As the use of angioplasty, stent delivery, drug delivery and other intravascular procedures continues to increase, there is a continuing need to provide new, reinforced multi-lumen catheters with improved trackability and pushability qualities and which can be easily manipulated for guide wire exchanges.

SUMMARY OF THE DISCLOSURE

An improved multi-lumen, reinforced catheter or shaft is disclosed. The shaft can be used for applications other than as a catheter where a multiple lumens are needed.

DETAILED DESCRIPTION OF THE PRESENTLY PREFERRED EMBODIMENTS

Figure 1:
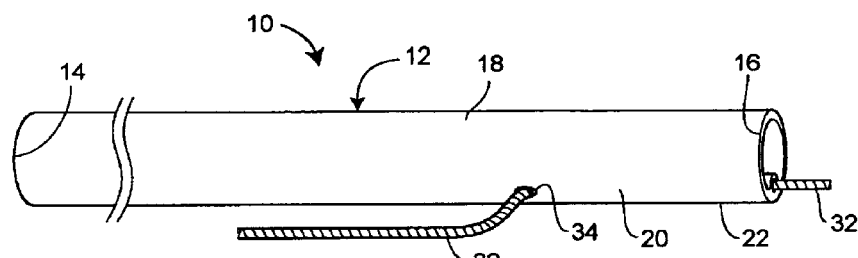
FIG. 1 is a partial side view of a disclosed catheter assembly.
Figure 2:
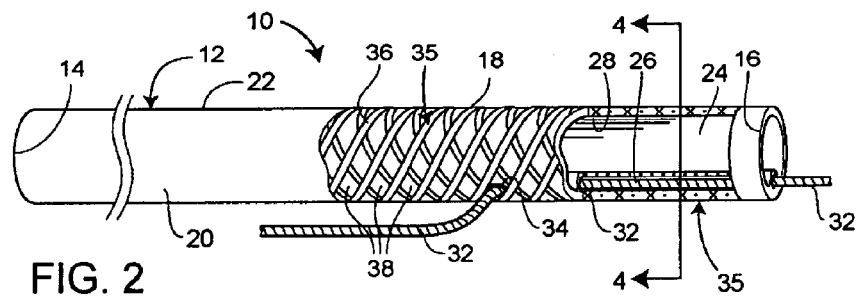
FIG. 2 is a partial side and longitudinal cross-sectional view of the catheter assembly of FIG. 1.
Figure 3:
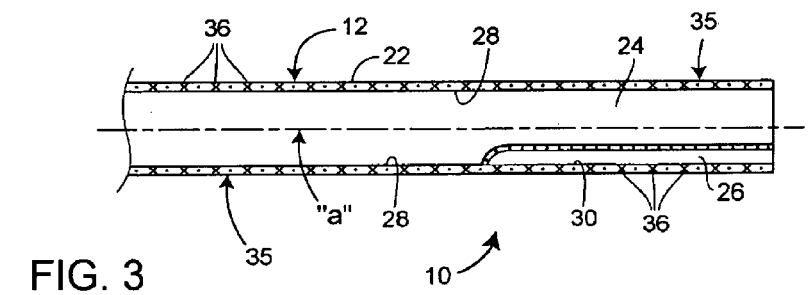
FIG. 3 is a partial longitudinal cross-sectional view of the catheter shaft of the catheter assembly in FIG. 1.

Referring now to FIGS. 1–3, a medical tubing or shaft 10 comprising an elongated tubular member 12 is shown. The shaft 10 has a proximal end 14, a distal end 16 and a middle section 18 between the proximal end 14 and the distal end 16. Additionally, the shaft 10 is comprised of a tubular wall 20 having an outer surface 22 and defining a main or first lumen 24 and an accessory or second lumen 26. The first lumen 24 has a first inner surface 28, and the second lumen 26 has a second inner surface 30 (see FIG. 3). The first lumen 24 can be used for balloon inflation or deflation, irrigation, delivery of drugs or other treatments and the facilitation of insertion of other surgical devices, such as an angioscope (not shown). The second lumen 26 can be used for accommodating for a guide wire 32, the delivery of drugs or other uses where a smaller lumen is required.

As shown in FIGS. 1–3, the first lumen 24 extends throughout the longitudinal length of the tubular member 12 between the proximal end 14 and the distal end 16. The second lumen 26 is parallel to the longitudinal axis "a" (See FIG. 3) of the first lumen 24 and can extend only through a portion of the distance between the proximal end 14 and the distal end 16 of the tubular member 12 or substantially along the entire length of the member 12. As shown in FIGS. 1–3, the second lumen 26 extends between the distal end 16 of the tubular member 12 and a side port 34 disposed in the outer surface 22 of the tubular wall 20. A guide wire system with only distal end access to the catheter is referred to as a single-operator exchange system or a rapid exchange system as discussed above. In the embodiment shown in FIGS. 1–3, the guide wire 32 can enter the second lumen 26 at the distal end 16 and exit the second lumen 26 at the side port 34. The side port 34 can be disposed in the middle section 18 of the tubular member 12 distal to the proximal end 14 of the tubular member 12.

FIG. 3 best illustrates a short guide wire lumen or second lumen 26 which is used in a rapid exchange system. The second lumen 26 is advantageous because it allows the guide wire 32 to remain protected in its own lumen for the entire length of the distal portion of the tubular member 12. As is shown in FIGS. 2 and 3, the tubular wall 20 includes a reinforcing element 35 that supports or reinforces the tubular member 12. Generally, such a reinforcing element 35 may be comprised of a braid of high-strength fibers, stainless steel wires, ribbons of a super-elastic alloy, etc. Specifically, the embodiments of the shaft 10 shown in FIGS. 2 and 3 have a reinforcing element 35 comprised of one or more braided elements 36. As shown in this embodiment of shaft 10, the braided elements 36 are a plurality of tubular or ribbon-like constructions which are woven radially in an in-and-out fashion as they cross to form a tubular structure. The braided elements 36 in this embodiment may be made from a plurality of metallic wires and metallic ribbons.

A majority of the metallic wires and metallic ribbons are comprised of a member of a class of alloys known as super-elastic alloys which include the class of titanium/nickel materials known as nitinol. Additionally, the braided elements 36 could be made of a non-metallic composition, such as, for example, a high performance material from the group including polyarimids (e.g. KEVLAR®) and carbon fibers. Various materials which may be used for the braided elements 36 are discussed at length in U.S. Pat. No. 5,782,811 and are incorporated herein by reference. Super-elastic alloys are desirable because they possess exceptional strength to resist kinking and to recover from kinking, even in vivo, should kinking occur.

Further, the reinforcing element 35 that comprises of these alloys is desirable because it reinforces the tubular wall 20 to enhance the trackability and pushability of the tubular member 12. It is beneficial to utilize the braided elements 36 because they are small in diameter and therefore do not contribute significantly to the thickness of the tubular wall 20 which makes the tubular member 12 more flexible and better able to traverse the tortuous pathways of the vascular system. The braided reinforcing element 35, as shown in the embodiments of FIGS. 2 and 3, is additionally advantageous because it improves the axial strength or pushability of the catheter 10. By varying the spacing between adjacent braid elements 36 or the size of the interstices 38 (i.e., the pick or count of the braid), the stiffness of the catheter 10 can be varied along the length of the catheter. More specifically, as the pick (or the number of warp or weft braid elements per inch) increases, the flexibility of the shaft 10 increases and the stiffness of the shaft 10 decreases; in contrast, as the pick decreases, the flexibility of the shaft decreases and the stiffness of the shaft 10 increases. As a result, a rigid reinforcement section (not shown) for the proximal portion of the catheter shaft 12 can be provided, and a more flexible reinforcement section (not shown) for the distal portion of the catheter shaft 12 can be provided. Such a flexible distal portion would allow the shaft 10 to more easily negotiate the curvatures within a vasculature system. Such a rigid proximal portion would enhance the pushability and steerability of the shaft 10. Further, the port 34 may be disposed in such a transition area where the pick of the braid 35 is being varied.

As shown in FIG. 2, the reinforcing element 35 has plurality of interstices 38 located between the braid elements 36. In this embodiment of shaft 10, the side port 34 is disposed in one of the plurality of interstices 38. Because the side port 34 can be placed through one of the interstices 38, the braided elements 36 of reinforcing element 35 remain continuous and are not interrupted like many of the braided catheters in current use. For example, in many catheters, the braided tubing is terminated before the side guide wire port. Then a heavy walled plastic tubing, in which the side port is disposed, is bonded to the braided tubing thereby creating a transition area from braided tubing to plastic tubing. This transition area between the braided tubing and the plastic tubing is susceptible to kinking. Thus, it is desirable to have a braided catheter tubing, as shown in FIGS. 2 and 3, that extends continuously from the proximal end to the distal end of the catheter or at least past the side port 34.

The reinforcing element 35 may additionally be comprised of a spirally wound material (not shown). The spirally wound material may have spaces or interstices between each spiral of the reinforcing element, and the side port 34 may be placed through one of the interstices between the spirals of the reinforcing element.

Finally, as shown in FIG. 3, a third lumen 26a is shown in phantom. A third lumen 26a can be used for the injection of contrast, saline or drugs through the port 34a. Instead of injecting contrast or drugs through the main lumen 24, the smaller lumen 26a can be used for a more efficient delivery and less waste. Further, purging air from the smaller lumen 26a is fast and easy. Also, contrast will flow through the lumen 26a more easily than through a lumen 24 that also accommodates a treatment device such as a stent.

Figure 4:
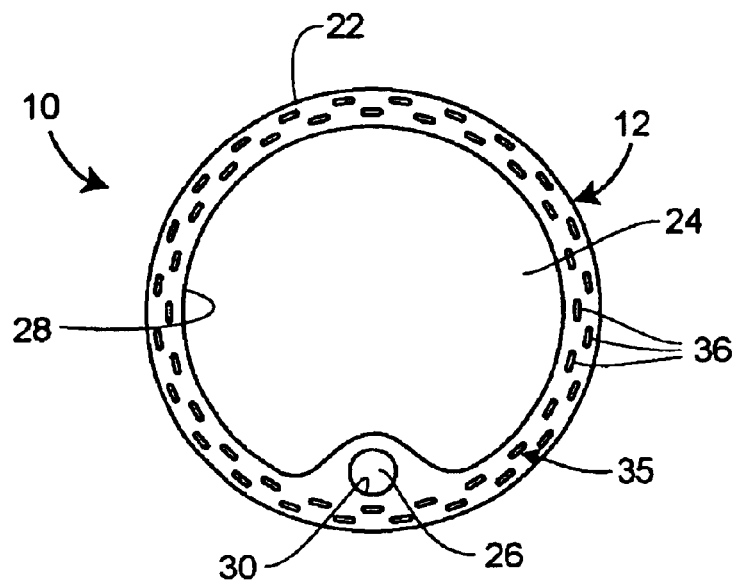
FIG. 4 is a transverse cross-sectional view of the catheter shaft of the catheter in FIG. 1 taken along line 4—4 of FIG. 2.
Figure 5:
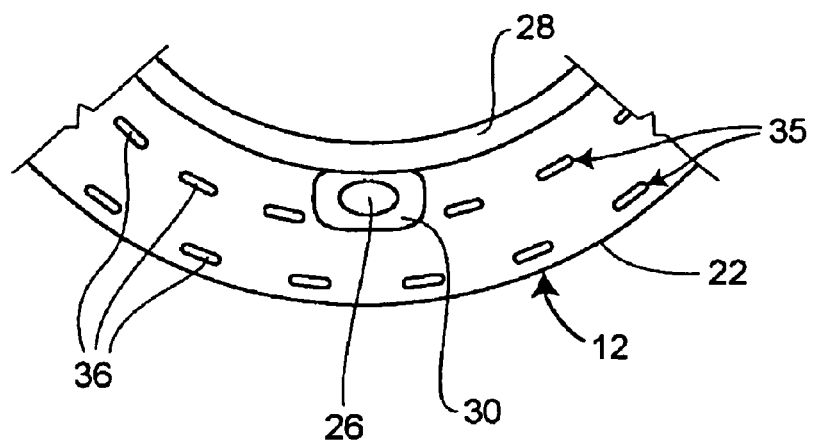
FIG. 5 is a magnified partial transverse cross-sectional view of an alternate embodiment of a catheter shaft.

As illustrated in FIG. 4, the first lumen 24 and the second lumen 26 are adjacent each other. In the embodiment shown, the diameter of the first lumen is greater than the diameter of the second lumen. However, in alternative embodiments, the first lumen 24 and the second lumen 26 may each have the same diameter, or the first lumen 24 may have a diameter that is less than the diameter of the second lumen 26. To accommodate a 0.035" guidewire, the lumen 26 would require a diameter of about 0.037". Lumen 24, on the other hand, would accommodate 4F to 12F devices and, therefore, would have a diameter ranging from about 0.055" to about 0.180". FIG. 5 shows the second lumen 26 disposed among the braided elements 36 of the reinforcing element 35. As illustrated, the inner surface 28 of the first lumen 24 is adjacent the inner surface 30 of the second lumen 26.

The inner surface 28 of the first lumen 24 is preferably made of polytetraflouroethylene ("PTFE"). The inner surface 30 of the second lumen 26 is preferably made of PTFE, poly ether ether ketone ("PEEK") or GRILAMID® because these materials are not tacky, they allow the guide wire to easily slide through second lumen 26, and do not degrade processing temperatures for PEBAX® or HYTREL® which can be used for the outer surface 22 in addition to polyester, nylon or some other polymer material having similar characteristics.

Figure 6:
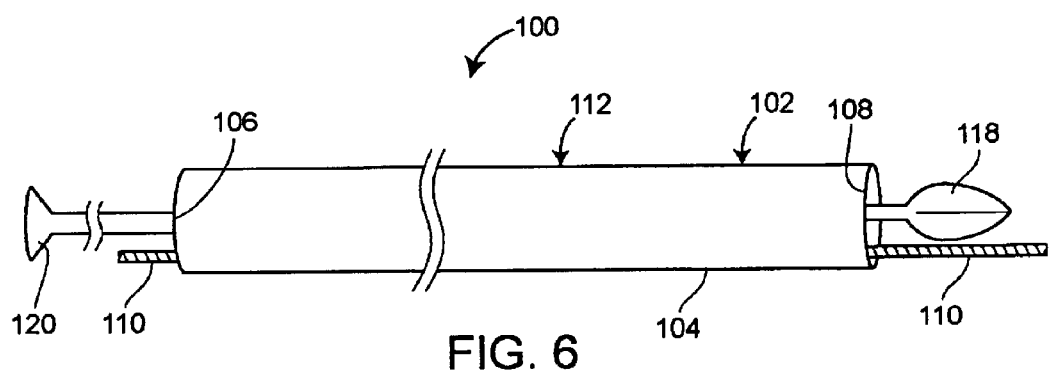
FIG. 6 is a partial side view of another disclosed catheter assembly.
Figure 7:
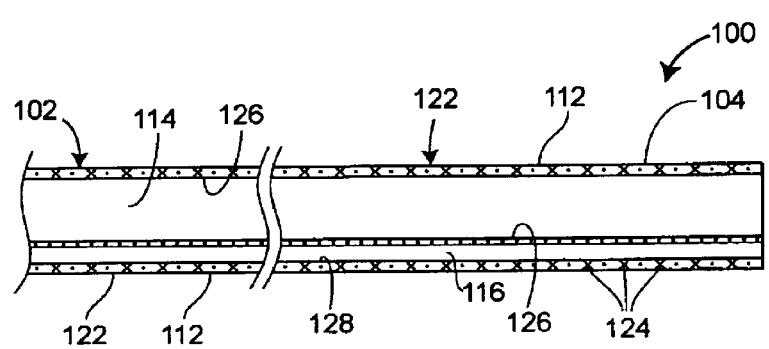
FIG. 7 is a partial longitudinal cross-sectional view of the catheter shaft of the catheter assembly of FIG. 6.

FIGS. 6 and 7 illustrate another catheter 100 having an elongate tubular member 102 which is a catheter used for over-the-wire guide wire exchange. The elongate member 102 has an outer surface 104, a proximal end 106 and a distal end 108. A guide wire 110 protrudes from the proximal end 106 and the distal end 108. The elongate tubular member 102 also has a tubular wall 112 which defines a first lumen 114 and a second lumen 116. The first lumen 114 and the second lumen 116 both extend throughout the length of the tubular member 102 between the proximal end 106 and the distal end 108.

As is shown in FIG. 6, a treatment device 118 is shown extending from the distal end 108 for insertion into the narrowed vessel(s) and having a proximal end 120 which extends from the proximal end 106 for control by the physician. As shown in FIG. 7, the first lumen 114 is greater in diameter than the second lumen 116. However, in alternate embodiments, the first lumen 114 and the second lumen 116 could be the same size or the first lumen 114 could be smaller in diameter than the second lumen 116. A reinforcing element 122 having braided elements 124 is disposed in the tubular wall 112. The first lumen 114 has a first inner surface 126, and the second lumen 116 has a second inner surface 128. The materials comprising catheter 100 can be the same as those disclosed in connection with catheter 10 described above.

Figure 8:
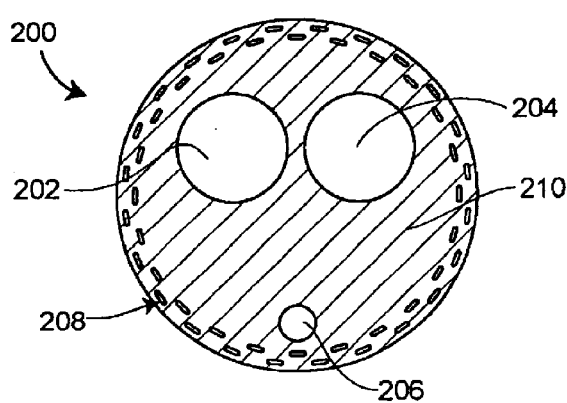
FIG. 8 is a transverse cross-sectional view of an alternate embodiment of a catheter shaft.

Another reinforced multi-lumen shaft is shown in FIG. 8. FIG. 8 illustrates a shaft 200 having a first lumen 202, a second lumen 204 and a third lumen 206. In this embodiment, any one of the three lumens may be designated the guide wire lumen. A reinforcing element 208 is disposed in a tubular wall 210. Catheter 200 is constructed similar to catheters 10 and 100 except that catheter 200 has three lumens. Hence, catheter 200 may be comprised of the same materials as catheters 10 and 100.

The catheter 200 may be made, for example, by placing a layer of PTFE over a first stainless steel support mandrel so that the interior lining of the PTFE fits snugly on the first mandrel. A second stainless steel support mandrel is then covered with a layer of a selected polymer of either PTFE, PEEK or GRILAMID® so that the polymer fits tightly around the second mandrel. The first PTFE-covered mandrel is then placed adjacent the second polymer-covered mandrel. The first and second adjacent mandrels are then slid into a length of braided wire elements so that the braided wire elements fit tightly to the exterior surfaces of the two covered mandrels. In this embodiment, the second polymer-covered mandrel lies adjacent the first PTFE-covered mandrel extending between the intended proximal end and the intended distal end of the tubing covering the first mandrel. A third polymer is then layered over the assembly. This third polymer which may comprise either PEBAX®, polyester, nylon or some other material having similar preferred characteristics, is placed over the braided elements and the two polymer-covered mandrels.

This entire assembly is then placed into a length of flourinated ethylene propylene ("FEP") or other heat-shrink tubing for a final thermal-processing step at a suitable temperature for a suitable time duration in an oven. The heat-shrink tubing is used to compress the aforementioned layers together during the thermal-processing step. The thermal-processing step allows the outer layer of tubing to reflow and form tightly about the braided elements and the two polymer-covered mandrels. Upon completion of the thermal-processing, the entire assembly is removed from the oven and the outer layer of heat-shrink tubing is removed and discarded. Finally, the two stainless steel support mandrels are removed to form the lumens 202, 204 as shown in FIG. 8. Of course, a third support mandrel can be employed to form the third lumen 206.

To create a multi-lumen catheter 10 for use in a rapid exchange system, the above process is slightly modified. As described above with the over-the-wire construction, the catheter 10 may be made, for example, by placing a layer of PTFE over a first stainless steel support mandrel so that the interior lining of the PTFE fits snugly on the first mandrel. A second stainless steel support mandrel is then covered with a layer of polymer, either PTFE, PEEK or GRILAMID®, so that the polymer fits tightly around the second mandrel. The first PTFE-covered mandrel is then placed adjacent the second polymer-covered mandrel. The first and second polymer-covered mandrels are then slid into a length of braided wire elements so that the braided wire elements fit tightly to the exterior surfaces of the first and second covered mandrels. Then, the second polymer-covered mandrel is threaded or woven through one or multiple braid interstitials to provide the port 34 as shown in FIGS. 1 and 2.

Next, a third polymer which comprises either PEBAX®, polyester, nylon or some other material having similar preferred characteristics, is placed over the braided elements and the two polymer-covered mandrels. The intended proximal end of the second polymer-covered mandrel passes through one of the braid interstitials to the exterior of the braids punching through the outer polymer layer to form a side port exit for a guide wire. This entire assembly is then placed into a length of FEP or other heat-shrink tubing for a final thermal-processing step at a suitable temperature for a suitable time duration in an oven. The heat-shrink tubing is used to compress the aforementioned layers together during the thermal-processing step.

The thermal-processing step allows the outer layer of tubing to reflow and form tightly about the braided elements and the two polymer-covered mandrels. Upon completion of the thermal-processing, the entire assembly is removed from the oven and the outer layer of heat-shrink tubing is removed and discarded. The exterior portion of second polymer-covered mandrel which protrudes from the catheter is trimmed so that the tubing is flush with the outer surface of the outer layer of tubing. Finally, the two stainless steel support mandrels are removed, leaving the finished, rapid exchange type, reinforced multi-lumen catheter 10.

What is claimed is:

1. A medical tubing comprising:
   an elongate tubular member having a proximal end, a distal end and a tubular wall extending therebetween which defines a first lumen, the first lumen comprising an inlet and an outlet,
   the elongate tubular member further comprising a second lumen extending through at least a portion of the tubular member, the second lumen comprising an inlet and an outlet defined by a first side port,
   the tubular wall including a reinforcing element that surrounds at least a portion of the first lumen, the reinforcing element being a braided structure comprising a plurality of woven ribbons with interstices disposed between the ribbons,
   the reinforcing element surrounding and overlapping at least a portion of the second lumen, and the first side port extending through the tubular wall to the second lumen and connecting an outer surface of the tubular member to the second lumen, the side port also extending through one of the interstices of the reinforcing element.

2. The medical tubing of claim 1, wherein the braided structure comprises a super-elastic alloy.

3. The medical tubing of claim 2, wherein the super-elastic alloy comprises a nickel-titanium alloy.

4. The medical tubing of claim 1, wherein the braided structure comprises a polymer.

5. The medical tubing of claim 1, wherein the braided structure comprises a metal.

6. The medical tubing of claim 1, wherein the tubular member comprises a polymer.

7. The medical tubing of claim 6, wherein the polymer is polytetrafluoroethylene.

8. The medical tubing of claim 1, wherein the first lumen has a first diameter and the second lumen has a second diameter, the first diameter being greater than the second diameter.

9. A medical tubing comprising:

an elongate tubular member having a proximal end, a distal end and a tubular wall extending therebetween which defines a first lumen, the first lumen comprising an inlet and an outlet, the elongate tubular member further comprising a second lumen extending through at least a portion of the tubular member, the second lumen comprising an inlet and an outlet defined by a first side port, the tubular wall including a reinforcing element that surrounds at least a portion of the first lumen, the reinforcing element being a braided structure comprising a plurality of woven ribbons with interstices disposed between the ribbons, the reinforcing element surrounding and overlapping at least a portion of the second lumen, and the first side port extending through the tubular wall to the second lumen and connecting an outer surface of the tubular member to the second lumen, the side port extending through one of the interstices of the reinforcing element, wherein the braided structure further comprises a first pick for a proximal portion of the braided structure disposed between the side port and the proximal end of the tubular member that is less than a second pick for a distal portion of the braided structure disposed between the side port and the distal end of the tubular member.

10. A method of making a multi-lumen catheter, the method comprising the steps of:

covering a first mandrel with a first polymer;

covering a second mandrel with a second polymer;

placing the first mandrel adjacent to the second mandrel;

sliding a length of a tubular reinforcing element around the first mandrel and the second mandrel, the tubular reinforcing element being a braided structure that is woven from a plurality of ribbons with interstices disposed between the ribbons;

inserting an end of the second mandrel through one of the interstices;

covering the tubular reinforcing element with an outer tubing;

puncturing the outer tubing with the end of the second mandrel;

covering the outer tubing with a heat-shrink tubing;

heating the heat-shrink tubing;

removing and discarding the heat-shrink tubing; and removing the first mandrel and the second mandrel.

11. The method of claim 10, wherein the first polymer is polytetraflouroethylene.

12. The method of claim 10, wherein the braided structure comprises a super-elastic alloy.

13. The method of claim 12, wherein the super-elastic alloy comprises a nickel-titanium alloy.

14. The method of claim 10, wherein the braided structure comprises a metal.

15. The method of claim 10, wherein the braided structure comprises a non-metal.

* * * * *